United States Patent [19]
Seidel et al.

[11] Patent Number: 5,591,888
[45] Date of Patent: Jan. 7, 1997

[54] PROCESS FOR PRODUCING TERT.-BUTYL CHLOROACETATE

[75] Inventors: Andreas Seidel, Köln; Dieter Peters; Norbert Weferling, both of Hürth-Efferen; Dimitrios Mouratidis, Frechen, all of Germany

[73] Assignee: Hoechst AG, Frankfurt am Main, Germany

[21] Appl. No.: 527,543

[22] Filed: Sep. 13, 1995

[30] Foreign Application Priority Data

Sep. 27, 1994 [DE] Germany ............... 44 33 444.9

[51] Int. Cl.$^6$ ............................................. C07C 69/63
[52] U.S. Cl. ............................................. 560/226
[58] Field of Search ................................. 560/226

[56] References Cited

PUBLICATIONS

Beilstein—1753006—1975 Preparation by Pavlov, Preparation by Closkey et al.
Johnson, W. S., et al, *J. Amer. Chem. Soc.* 75:4995–5001 (see p. 4998) (1953).
Fieser, L. u. M., *Organic Chem.*, p. 575 (1965).

*Primary Examiner*—Samuel Barts
*Attorney, Agent, or Firm*—Connolly & Hutz

[57] ABSTRACT

To produce tert-butyl chloroacetate by addition of chloroacetic acid to isobutene, the reaction is carried out in the absence of catalysts and solvents in a pressure vessel at a temperature of 80° to 110° C. under the pressure which establishes itself of 3 to 12 bar over a period of 1 to 12 hours. After the pressure vessel is cooled, the cooled product mixture is withdrawn and it is worked up by distillation under reduced pressure without prior neutralization.

3 Claims, No Drawings

PROCESS FOR PRODUCING TERT.-BUTYL CHLOROACETATE

Tert-butyl chloroacetate is an organic intermediate which is used in particular for the preparation of glycide esters from ketones in the Darzens condensation. The corresponding glycide esters may themselves be converted by decarboxylation into aldehydes which have one more carbon atom than the ketone used (cf. e.g. L. u. M. Fieser, Organische Chemie [Organic Chemistry] (1965), p. 575). Such extensions of a molecular skeleton are frequently a component of organic syntheses, e.g. of pharmaceuticals.

However, broad application of tert-butyl chloroacetate has not been possible hitherto because of a lack of an industrially attractive preparation process. In the relevant literature, only laboratory methods are described, thus e.g. the esterification of chloroacetic acid with tert-butanol and dicyclohexyl carbodiimide, catalyzed by 4-dimethylaminopyridine, or the reaction of chloroacetyl chloride with tert-butanol in benzene in the presence of activated alumina or with tert-butanol and dimethylaniline. In addition, e.g. W. S. Johnson et al., J. Amer. Chem. Soc. 75 (1953), p. 4998 describe the addition of chloroacetic acid to isobutene, catalyzed by sulfuric acid in dioxane at room temperature.

All of the processes mentioned make requirements which impede conversion to the industrial scale. Thus costly auxiliaries are used stoichiometrically which are consumed in the reaction and cannot be recycled or catalysts are used which complicate operation of the process.

The most expedient mass balance of the three process variants is given by the addition of chloroacetic acid to isobutene in which neither water nor hydrogen chloride is formed. It is a disadvantage of this process that sulfuric acid is used as a catalyst which catalyzes the dimerization and trimerization of isobutene. These side-reactions lead to significant losses of selectivity in said process. To remove sulfuric acid, it is neutralized with aqueous potassium hydroxide solution.

However, this process step leads to the loss of considerable-amounts of unreacted chloroacetic acid which is likewise neutralized and transferred to the aqueous phase.

The object was therefore to find an industrially feasible process for the preparation of tert-butyl chloroacetate which avoids said disadvantages.

In the study of the addition of chloroacetic acid to isobutene we surprisingly observed that the reaction can be carried out without a catalyst (such as sulfuric acid), auxiliaries and solvents with high space-time yields if the reaction temperature is elevated. The addition process modified in this manner proceeds with an astonishingly high yield, calculated on converted isobutene (so-called isobutene selectivity) and thus gives considerable advantages which enable conversion to the industrial scale. Thus the separation of the product mixture is simplified since only unreacted chloroacetic acid need be separated off from the reaction solution and a further rectification by distillation of the product is not necessary. It has been shown in this case that the separation by distillation of unreacted chloroacetic acid as bottom product does not lead to any significant losses of yield during the distillation and a storage-stable product results.

In detail, the invention now relates to a process for preparing tert-butyl chloroacetate by addition of chloroacetic acid to isobutene in a closed vessel under the pressure establishing itself, which comprises carrying out the reaction in the absence of catalysts and solvents in a pressurized vessel at a temperature of 80° to 110° C. under the pressure establishing itself of 3 to 12 bar over a period of 1 to 12, preferably 4 to 8 hours, cooling the pressure vessel, withdrawing the cooled product mixture and working it up by distillation under reduced pressure without prior neutralization.

Example 189 g (2 mol) of molten chloroacetic acid [94.5] were weighed out into a laboratory autoclave lined with a PTFE shell and equipped with a PTFE-encoated, magnetically driven multiple blade stirrer. By introducing the autoclave into an ice/salt bath, the autoclave was cooled and the chloroacetic acid frozen. At the same time, about 112 g (1.98 mol) of isobutene [57.1] were condensed into a receiver cooled by a dry ice/acetone cooling bath and transferred to the precooled autoclave, during which some of the isobutene evaporated. The autoclave was sealed and heated to 90° C., where an internal pressure of initially 10 bar established itself. Under intensive stirring, the reaction was continued for 6 hours at 90° C. After cooling to room temperature, 277.4 g of product solution were withdrawn from the autoclave and transferred to a rotary evaporator. The solution was distilled at a pressure of 50 mbar and the bath temperature was gradually increased to 90° C. 152.2 g of product were recovered as distillate containing 97.7% by weight (=989 mmol) of tert-butyl chloroacetate [151.6] and di- and triisobutene (equivalent to 24 mmol of isobutene) and 26 mmol of tert-butanol. In addition, in a dry ice/acetone cold trap, 29.7 g of unreacted isobutene were collected which contained 0.51 g of di and triisobutene (equivalent to 9 mmol of isobutene) and 0.45 g (3 mmol) of tert-butyl chloroacetate and were reused in the next batch. 95.4 g of highly pure (99.8% by weight) pale-red chloroacetic acid remained behind in the bottom of the rotary evaporator and were reused for the next batch.

In the following table the result is compared with that of W. S. Johnson et al., J. A. C. S. 75, p. 4998, right column (1953):

|  | Literature*) | Invention |
|---|---|---|
| Space-time yield [g/l.h] | 27 | 100 |
| Conversion of monochloroacetic acid [%] | 59 | 50 |
| Yield, calculated on converted isobutene [%] = selectivity | 83 | 94 |

*)Corrected by the content noted there of 7% polyisobutene.

We claim:

1. A process for preparing tert-butyl chloroacetate by addition of chloroacetic acid to isobutene in a closed vessel under pressure, which comprises carrying out the reaction in the absence of catalysts and solvents in a pressurized vessel at a temperature of 80° to 110° C. over a period of 1 to 12 hours, cooling the pressure vessel, withdrawing the cooled product mixture and distilling under reduced pressure without prior neutralization.

2. A process as claimed in claim 1, wherein the reaction is carried out over a period of 4 to 8 hours.

3. A process as claimed in claim 1, wherein the pressure in the closed vessel is 3–12 bar.

* * * * *